(12) United States Patent
McGowan

(10) Patent No.: US 6,346,143 B1
(45) Date of Patent: Feb. 12, 2002

(54) ODOR ADSORPTIVE FILTER FOR REFRIGERATORS AND FREEZERS

(76) Inventor: Kimberly F. McGowan, 503 N. Water's Edge Dr., Durham, NC (US) 27703

( * ) Notice: Subject to any disclaimer, the term of this patent is extended or adjusted under 35 U.S.C. 154(b) by 0 days.

(21) Appl. No.: 09/510,507

(22) Filed: Feb. 22, 2000

Related U.S. Application Data

(60) Provisional application No. 60/121,672, filed on Feb. 25, 1999.

(51) Int. Cl.[7] .............................................. B01D 53/04
(52) U.S. Cl. ........................ 96/117.5; 96/135; 96/138; 96/147; 96/151; 96/153; 96/154; 96/222
(58) Field of Search ................. 96/117.5, 134, 96/135, 138, 147, 148, 151, 153, 154, 222

(56) References Cited

U.S. PATENT DOCUMENTS

| | | | | |
|---|---|---|---|---|
| 1,675,228 A | * | 6/1928 | Schmidt | 96/147 |
| 2,001,828 A | * | 5/1935 | Smith | 96/147 |
| 2,117,570 A | * | 5/1938 | Philipp | 96/148 X |
| 2,206,705 A | * | 7/1940 | Newman | 96/148 X |
| 2,222,882 A | * | 11/1940 | Shames | 96/148 X |
| 2,581,684 A | * | 1/1952 | McKenzie | 96/151 |
| 2,693,864 A | * | 11/1954 | Ferro | 96/117.5 |
| 2,765,046 A | * | 10/1956 | Rondholz | 96/148 X |
| 3,266,973 A | * | 8/1966 | Crowley | 96/117.5 X |
| 3,309,849 A | * | 3/1967 | Ward | 96/134 |
| 3,739,558 A | * | 6/1973 | Hurson | 96/151 |
| 4,065,262 A | | 12/1977 | Petroff | 21/74 R |
| 4,118,226 A | * | 10/1978 | Bourassa | 96/222 |
| 4,433,024 A | * | 2/1984 | Eian | 96/153 X |
| 4,610,705 A | * | 9/1986 | Sarnosky et al. | 96/135 |
| 4,689,058 A | * | 8/1987 | Vogt et al. | 96/135 |
| 4,863,499 A | * | 9/1989 | Osendorf | 96/134 |
| 4,948,567 A | | 8/1990 | Atarashiya | 422/122 |
| 4,995,556 A | | 2/1991 | Arnold, III | 239/57 |
| 5,062,272 A | | 11/1991 | Burns | 62/78 |
| 5,129,929 A | * | 7/1992 | Linnersten | 96/117.5 |
| 5,226,937 A | * | 7/1993 | Linnersten et al. | 96/117.5 |
| 5,288,298 A | * | 2/1994 | Aston | 96/135 |
| 5,417,743 A | * | 5/1995 | Dauber | 96/117.5 X |
| 5,422,078 A | | 6/1995 | Colon | 422/123 |
| 5,468,447 A | | 11/1995 | Bermas | 422/5 |
| 5,492,675 A | | 2/1996 | Brizard | 422/122 |
| 5,593,482 A | * | 1/1997 | Dauber et al. | 96/117.5 |
| 5,616,169 A | * | 4/1997 | De Ruiter et al. | 96/153 X |
| 5,662,728 A | * | 9/1997 | Groeger | 96/153 |

FOREIGN PATENT DOCUMENTS

| | | | | |
|---|---|---|---|---|
| DE | 3443274 | * | 5/1986 | 96/153 |
| GB | 2238731 | * | 6/1991 | 96/138 |
| JP | 3-95379 | | 4/1991 | |
| JP | 5-18657 | | 1/1993 | |

* cited by examiner

Primary Examiner—Robert H. Spitzer
(74) Attorney, Agent, or Firm—Richard C. Litman

(57) ABSTRACT

An odor adsorptive filter for use in refrigerators, freezers, and/or other cold storage units, is removably securable to one of the interior walls or panels of the unit and adsorbs odoriferous matter from spoiled foods, strong food odors, etc. as the air within the unit circulates. The present filter comprises a filter housing which is removably secured within the refrigerator or freezer by suction cups which adhere securely to the smooth surfaces of such units, without damage or marring of the surface. The filter element is in turn removably secured within the filter housing, for replacement as necessary. The filter element comprises a woven or nonwoven fiber material, with the fibers being coated or impregnated with an odor adsorbent material such as baking soda and/or activated carbon in some form. The filter element, or the housing, may also include a pleasant scent which will permeate the air in the cold storage device as unpleasant odors are adsorbed by the filter element. The filter element may also include an indicator for showing when replacement of the element is needed. The replacement indicator may be a device which changes color as the adsorptive properties of the filter element are saturated or depleted.

18 Claims, 8 Drawing Sheets

ODOR ADSORPTIVE FILTER FOR REFRIGERATORS AND FREEZERS

REFERENCE TO RELATED PATENT APPLICATION

This application claims the benefit of U. S. Provisional Patent Application Serial No. 60/121,672, filed on Feb. 25, 1999, originally titled "Space-Saving And Odor Absorbing Filter."

BACKGROUND OF THE INVENTION

1. Field of the Invention

The present invention relates generally to air filtration and deodorizing devices, and more specifically to a portable device for removably installing in a refrigerator, freezer, or similar cold food storage unit. The present filter device captures objectionable odors in a replaceable treated filter removably disposed within a housing, which is in turn removably installed within the refrigerator or freezer.

2. Description of the Related Art

Food spoilage is a recognized occurrence from time to time in virtually any refrigerator, freezer, or cold storage unit. Even when no power loss occurs, food can still spoil in the above freezing temperatures of a refrigerator, with unpleasant odors being the unfortunate result. Even when no spoilage occurs, the placement of strong and uncomplimentary foods in the confines of a refrigerator, will lead to unpleasant scents throughout the contents.

Accordingly, various means have been developed in the past to reduce or eliminate unpleasant odors in various cold storage devices. Perhaps the most common means known is the simple placement of an open box of baking soda in the interior of the refrigerator or freezer, with the compound serving to absorb odors as air circulates through the cold storage unit. Other devices have been developed as well, but all of the various devices of the prior art known to the present inventor, suffer from one or more drawbacks in terms of odor reduction, portability, cost and complexity, or in some other manner.

Accordingly, a need will be seen for an odor adsorptive filter for installation in a refrigerator, freezer, or other cold storage device as desired. The filter device must be portable for ease of installation and removal, must take up little room in order to avoid loss of interior volume in the unit, and must provide for the adsorption and removal of odor producing compounds within the interior volume of the unit. Moreover, the present invention may also provide for the addition of a pleasant scent to the interior air of the cold storage device, if so desired, and also provide an indication of saturation or loss of adsorptive capabilities for the adsorptive filter which is installed within the filter device.

A discussion of the related art of which the present inventor is aware, and its differences and distinctions from the present invention, is provided below.

U.S. Pat. No. 4,065,262 issued on Dec. 27, 1977 to Mitchell Petroff, titled "Filter And Air Freshener Apparatus," describes a furnace or air conditioning filter having a series of scent vials therein. One or more of the vials may be opened to deploy a scent through the air as it circulates through the filter. The Petroff device cannot be deployed within the relatively small confines of a refrigerator or freezer, without taking up an inordinate amount of the interior volume. Moreover, even if the Petroff filter were placed within a refrigerator or the like, it would do nothing to absorb unpleasant odors within the unit. The Petroff filter is a conventional heating or air conditioning filter which does nothing more than filter dust and the like from the air, with a means of spreading a scent through the air being added.

U.S. Pat. No. 4,948,567 issued on Aug. 14, 1990 to Kousuke Atarashiya, titled "Deodorizer For Refrigerators Or The Like," describes a system which is built in to the air circulation system within a refrigerator and freezer unit. The device includes both adsorbent materials (activated charcoal, etc.) and rare earth catalytic elements, and is installed adjacent the heating element of the defroster system. During normal operation the adsorbent elements capture odors circulating through the system. When the defrost cycle operates, the catalytic elements are heated by the defrost cycle heater, and serve to oxidize and decompose elements trapped by the adsorbents. The elements and function of the Atarashiya system require its permanent installation; they cannot be replaced without considerable effort and disassembly of the unit.

U.S. Pat. No. 4,995,556 issued on Feb. 26, 1991 to Benjamin L. Arnold III, titled "Unitized Sodium Bicarbonate Deodorizer," describes a deodorizing device comprising a series of three perforated concentric shells, each including a quantity of sodium bicarbonate (baking soda) therein. In another embodiment, the baking soda is provided in the form of solid cakes of various shapes. The Arnold, III deodorant devices are essentially throwaway units at the ends of their lives, with no provision for changing the deodorant substance within the container being provided by Arnold, III. Moreover, Arnold, III does not disclose the saturation or impregnation of a fiber matrix with an odor adsorbent material, nor any means of determining when the material requires changing, as provided by the present invention.

U.S. Pat. No. 5,062,272 issued on Nov. 5, 1991 to Marsha L. Burns, titled "Refrigerator Or Freezer Freshening Device And Process," describes a device comprising a canister containing baking soda and/or activated charcoal, along with a scent. As in the Arnold, III device discussed immediately above, the Burns air freshener does not provide for replacement of the adsorbent material within the container; the entire container and contents must be discarded when the contents have expired. Moreover, while Burns provides means for attaching her device to the interior wall of a refrigerator or the like, she uses an adhesive. When such adhesive attachment is removed, it leaves an adhesive residue which must be removed. The present air freshener device uses suction cups for removable attachment to a refrigerator or freezer interior.

U.S. Pat. No. 5,422,078 issued on Jun. 6, 1995 to Amber M. Colon, titled "Apparatus For Providing A Scent," describes a holder with orifices therethrough, and a removably replaceable scented insert for the holder. The insert merely contains a scent for distribution from the orifices of the holder; no means of adsorbing odors is disclosed by Colon. The scented insert also differs in construction from the adsorbent insert of the present invention, in that Colon uses a relatively dense thermoplastic material, while the present invention uses a woven or nonwoven fiber insert, with the fibers being coated with the adsorbent material to expose the maximum practicable surface area of adsorbent to the ambient air.

U.S. Pat. No. 5,468,447 issued on Nov. 21, 1995 to Edward M. Bermas, titled "Refrigerator Freshener," describes a container filled with activated carbon and zeolite (aluminum silicate) adsorptive materials. As in the case of the Arnold, III and Burns devices discussed further above, the entire assembly of container and contents of the Bermas device must be discarded when the contents have expired. In contrast, the container of the present air freshener device is reusable, with only the contents requiring replacement. Moreover, Bermas does not provide the means developed for the present invention of exposing the maximum practicable surface area of the adsorbent material to the air, by coating the fibers of a woven or nonwoven fiber mesh with the adsorbent material. Also, Bermas does not provide suction cup attachment for his device, to reduce the amount of space required for the device in the confined interior of a refrigerator or freezer.

U.S. Pat. No. 5,492,675 issued on Feb. 20, 1996 to Cyril J. C. Brizard, titled "Deodorant System," describes a disposable assembly comprising a container and odor adsorbent material therein. As in the Arnold, III, Burns, and Bermas devices discussed further above, the Brizard assembly must be discarded in its entirety when the adsorbent material therein is no longer effective. As noted above, the present device provides a reusable container for holding the replaceable adsorbent contents. Also, it is noted that Brizard provides means for indicating the replacement date, comprising a series of punch-out portions similar to the system used for indicating the purchase date on an automobile battery. This system is inconvenient in a device which may be secured to the rear interior wall of a refrigerator, where it cannot be readily viewed. The present air freshener device also provides a means for indicating the need for replacement of the adsorbent material, but does so by means of a tab or the like extending from the adsorbent, with the tab changing color according to the amount of adsorption activity.

Japanese Patent Publication No. 3-95,379 published on Apr. 19, 1991 to the Toshiba Corporation describes (according to the English abstract) a device which functions similarly to the device of the Atarashiya '567 U.S. Patent, discussed further above. The drawings appear to show an essentially identical device in both publications. The fact that such devices require permanent installation and are an integral part of the refrigerator and cannot be replaced, has been noted further above.

Finally, Japanese Patent Publication No. 5-18,657 published on Jan. 26, 1993 to Matsushita Refrigeration Company, Ltd. describes (according to the English abstract) a deodorizing system similar to those of the Atarashiya U.S. Patent and '379 Japanese Patent Publication discussed above. The same points of distinction raised in the discussion of those patent publications, are seen to apply to the '657 Japanese Patent Publication as well, particularly in view of the drawings in the '657 Japanese Patent Publication, which appear to show a device essentially similar to those of the Atarashiya U.S. Patent and '657 Japanese Patent Publication.

None of the above inventions and patents, either singly or in combination, is seen to describe the instant invention as claimed.

SUMMARY OF THE INVENTION

The present invention comprises an odor adsorptive filter for installation within a refrigerator, freezer, or other cold storage unit. The present filter contains an exchangeable odor adsorptive filter element, for capturing odoriferous particulates and molecules emanating from various foods stored in the unit. The present filter essentially comprises a filter housing which is removably secured to a back or side wall of the refrigerator or freezer interior (suction cups, etc.) and a filter element removably installed therein. The filter element comprises a woven or nonwoven fiber material, with the odor adsorptive material (baking soda, activated charcoal, etc.) coating the fibers to provide maximum exposed surface area for the adsorptive material.

The filter housing or element may also contain a pleasant scent if so desired, and preferably includes means for indicating when the adsorptive properties of the filter element have expired. The indicator means may comprise a colored tab extending from the element, with the tab changing, losing, or gaining color as it is exposed to the odoriferous particulate and molecules within the refrigerator or freezer. The present odor adsorptive filter provides a significant improvement in efficiency over conventional boxes or containers of baking soda which require shelf space and do not provide the efficiency of the coated fibrous elements of the present filter.

Accordingly, it is a principal object of the invention to provide an improved odor adsorptive filter for adsorbing odoriferous particulate and molecules from the air within a refrigerator, freezer, or other closed cold storage device.

It is another object of the invention to provide an improved odor adsorptive filter incorporating a removably installable filter housing and a filter element which is removably installable within the housing.

It is a further object of the invention to provide an improved odor adsorptive filter which filter element includes odor adsorptive materials selected from the group consisting of baking soda and activated carbon compounds.

Yet another object of the invention is to provide an improved odor adsorptive filter which filter element comprises a woven or nonwoven fibrous structure, with the odor adsorptive material coating the fibers of the filter element to maximize the surface area of the odor adsorptive material.

An additional object of the invention is to provide an improved odor adsorptive filter including means for providing a pleasant scent to the ambient air.

Still another object of the invention is to provide an improved odor adsorptive filter including means for indicating the expiration of the odor adsorptive material therein.

It is an object of the invention to provide improved elements and arrangements thereof in an apparatus for the purposes described which is inexpensive, dependable and fully effective in accomplishing its intended purposes.

These and other objects of the present invention will become apparent upon review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention comprises an odor adsorptive filter for installation within the interior cold storage compartment of a refrigerator, freezer, or other cold food storage device. The present filter invention serves to adsorb unpleasant odors which may emanate from spoiled foods, foods having strong scents or smells, etc. which often occur within the confines of such cold storage units for food.

Figure 1:
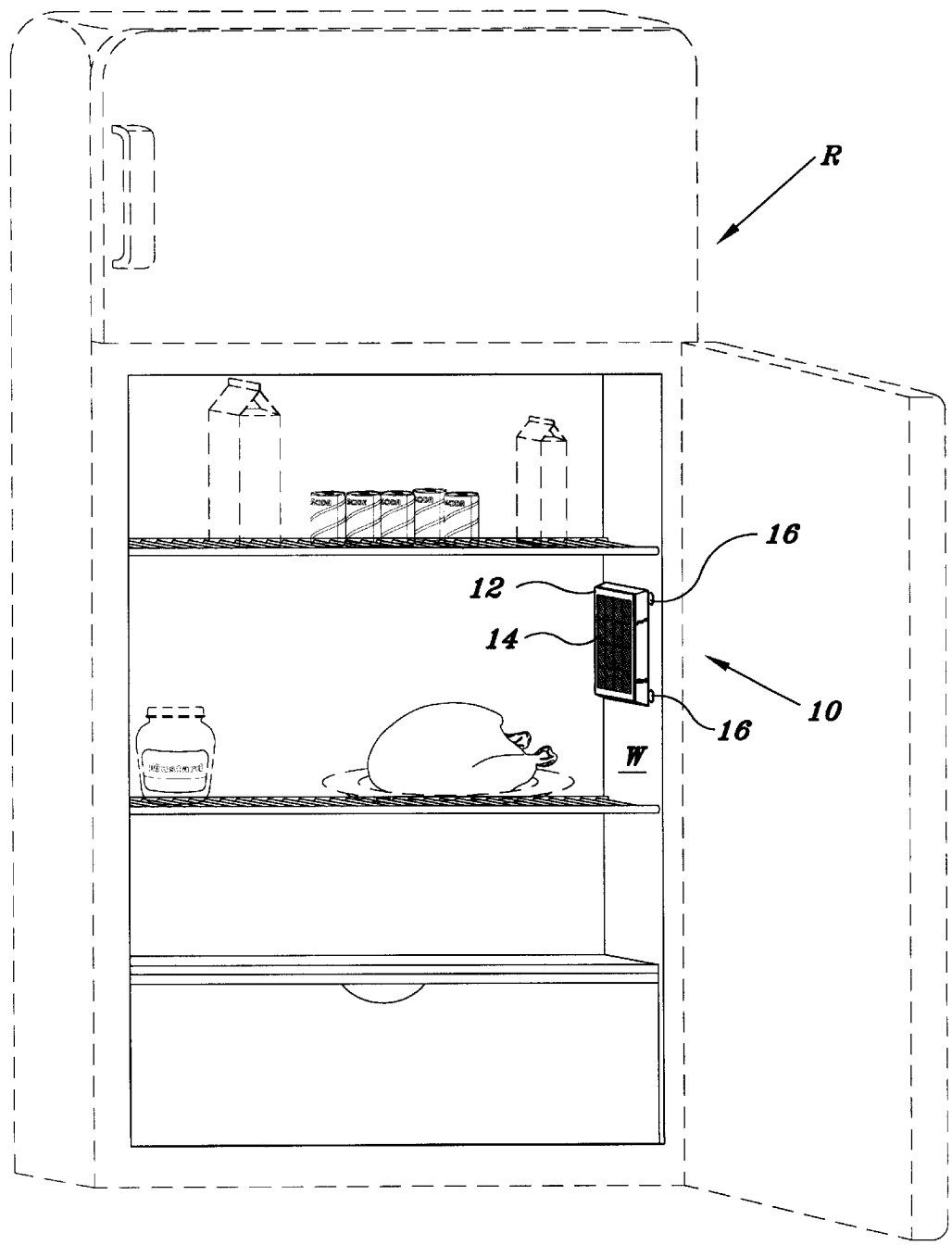
FIG. 1 is an environmental perspective view of a refrigerator showing the present odor adsorptive filter invention removably secured to an interior side wall therein.
Figure 2:
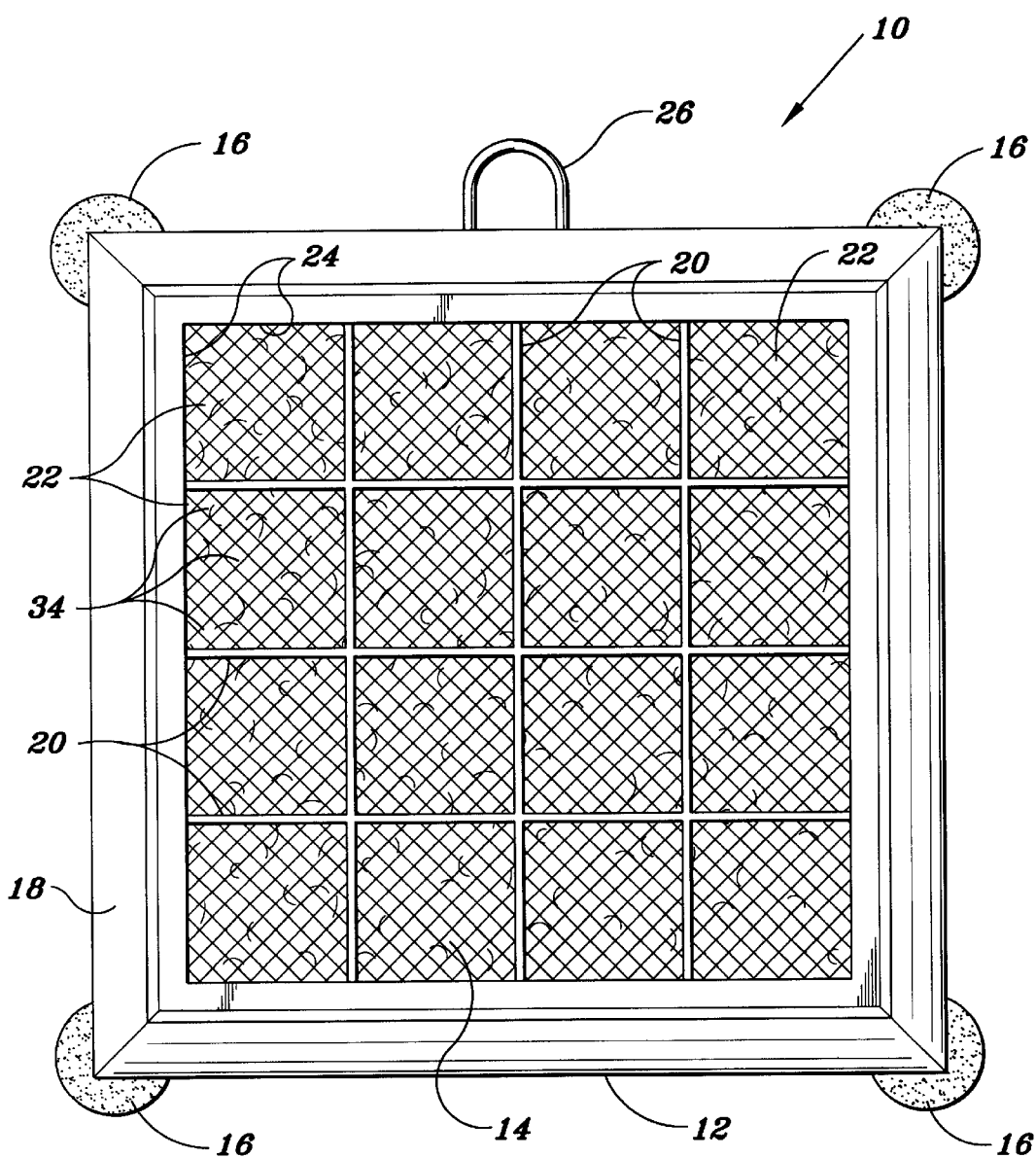
FIG. 2 is a front elevation view of a first embodiment of the present filter, showing its general configuration.
Figure 3:
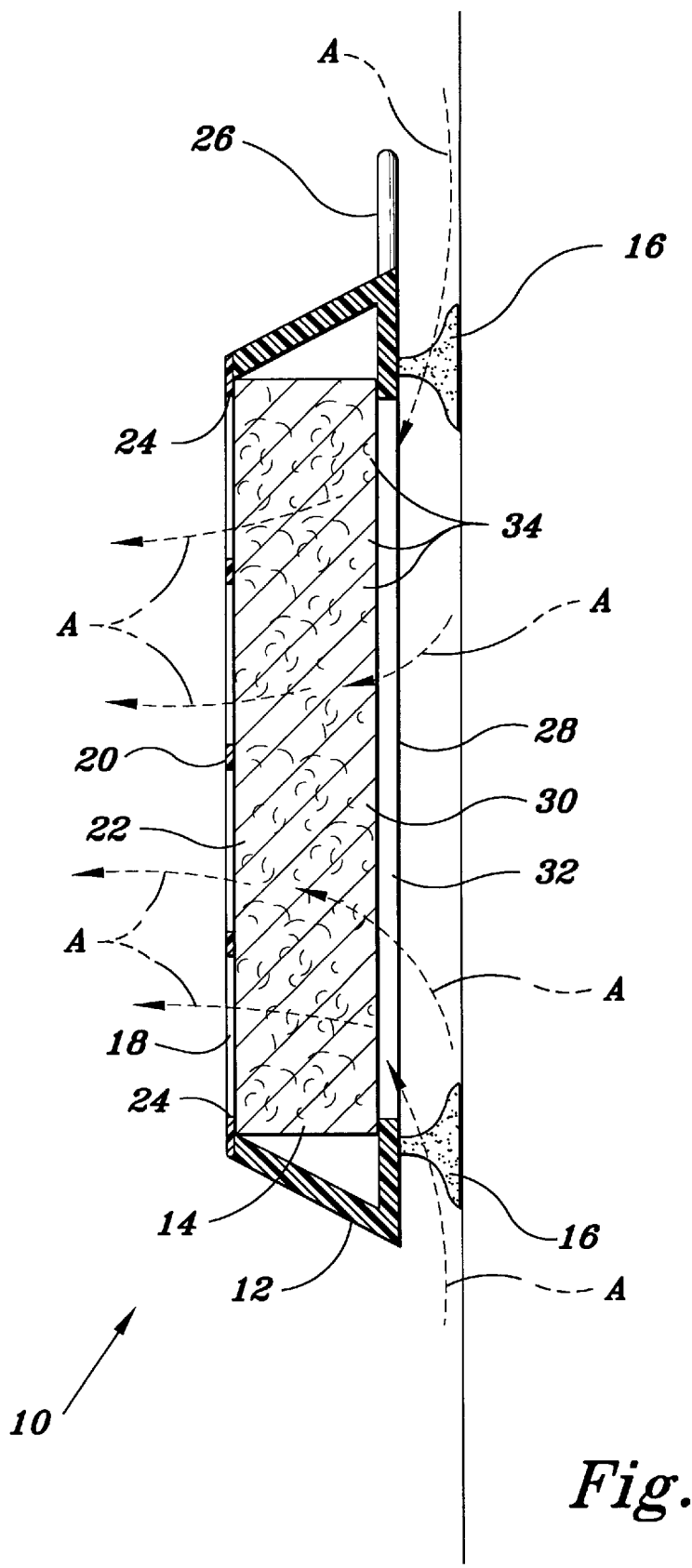
FIG. 3 is a side elevation view in section of the filter embodiment of FIG. 2, showing further details thereof.
Figure 4:
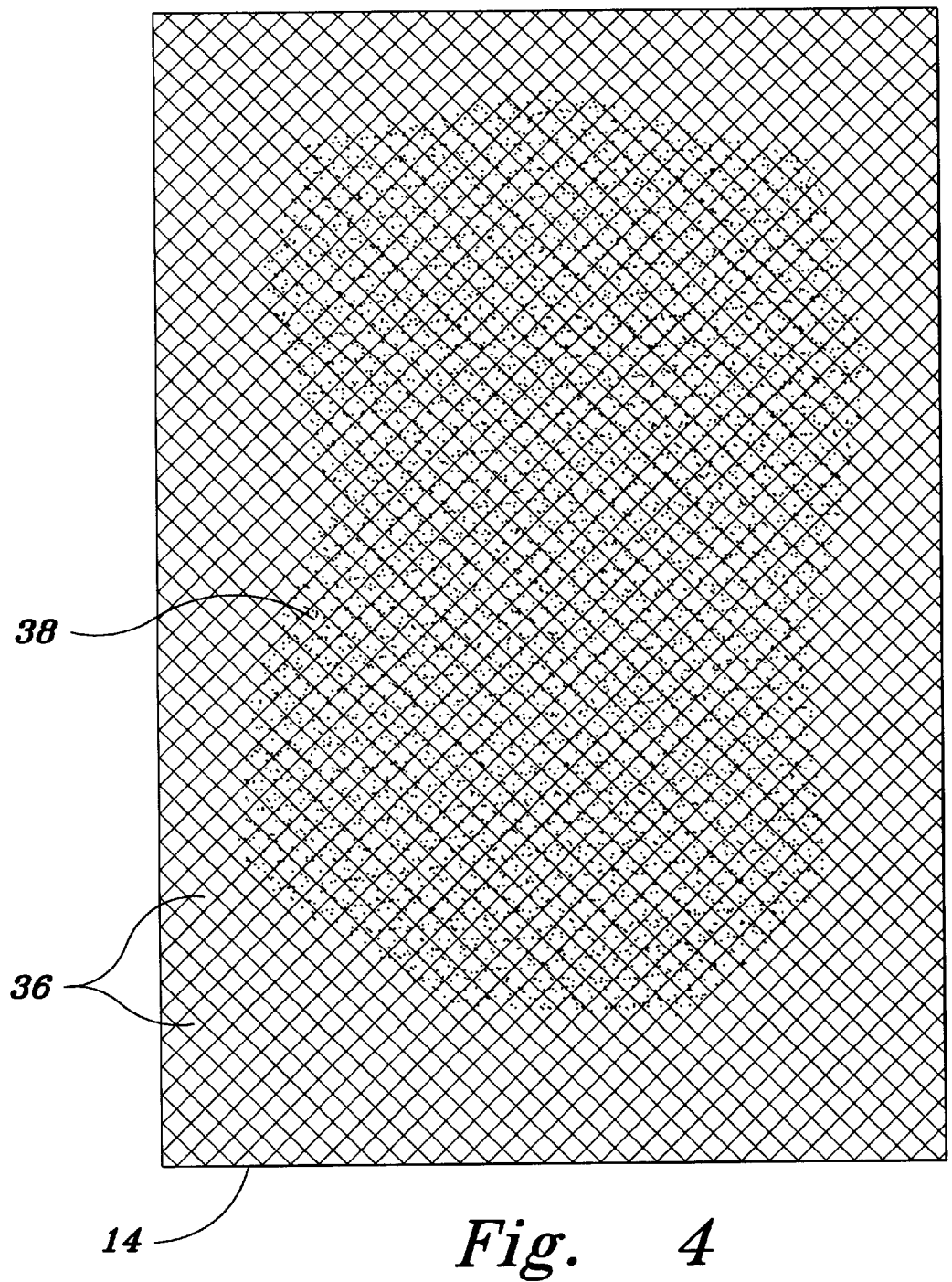
FIG. 4 is a schematic front elevation view of an exemplary filter element configured to fit a second embodiment filter of the present invention, showing its general features.

FIG. 1 provides an environmental view of one embodiment of the present filter 10 installed within a refrigerator R (shown in broken lines). The filter 10 essentially comprises a filter housing 12 which contains a filter element 14 therein. The housing 12 may be temporarily and removably secured to an interior wall W (any of the inner surfaces) of the refrigerator R by means of rearwardly disposed suction cups 16; other means may be provided as desired. FIGS. 2 and 3 provide additional detail for the filter 10 and components 12 and 14 of FIG. 1.

The front elevation view of FIG. 2 clearly illustrates the front panel 18 of the housing 12. The front panel 18 essentially comprises an open frame with a grid 20 disposed thereacross, to provide a series of air circulation passages 22 therethrough for the filter element 14 to communicate with the ambient air. The filter element 14 is retained behind the front panel 18 of the housing 12 by an inwardly facing lip 24 about the periphery of the front panel 18, and the grid structure 20 disposed across the front panel 18. A hanging loop 26 is also illustrated in FIGS. 2 and 3, serving as an alternative means for securing the filter assembly 10 within a refrigerator R or other area as desired.

The side elevation view in section of FIG. 3 illustrates further details of the present invention. In FIG. 3, the rear panel 28 is clearly shown opposite the front panel 18, with the two panels 18 and 28 defining a housing interior 30 therebetween for holding the filter element 14 therein. The rear panel 28 also includes at least one air circulation passage 32 therethrough.

The suction cup 16 removable attachment means provided for the present filter assembly 10, also serves to space the rear panel 28 away from its attachment wall W to some degree. This allows ambient air within the refrigerator or other cold storage unit, to flow between the rear panel 28 of the filter assembly 10 and its attachment wall W, whereupon some of this ambient air will pass through the passage(s) 32 in the rear panel 28, into the interior 30 and its filter element 14 contained therein, and outwardly through the passage(s) 22 of the front panel 18, as indicated by the air flow arrows A in FIG. 3. Circulation may be reversed, with air flowing from the front panel 18 through the filter 14 and out the rear panel 28, depending upon the circulation in the cooling unit, the location of the filter assembly 10 within the unit, and perhaps other factors. The critical point to note is that any closed system containing a gas (e.g., air) always has some convective circulation therein, which will eventually result in all of the air (and odoriferous matter carried thereby) circulating through the filter element 14 of the present invention, whereby the odoriferous elements are captured within the filter element 14 as discussed below.

The filter element 14 may be formed of any suitable porous material which is capable of holding a reasonable quantity (e.g., a few ounces or so) of odor adsorptive material therein. The filter element 14 may be formed of a nonwoven fibrous material 34, as indicated generally in FIGS. 2 and 3, or may be formed of a woven fibrous material 36, as indicated in FIGS. 4 through 8.

The porous fiber structural material 34 and/or 36 may comprise any suitable synthetic or natural fiber material. Glass fiber has been found to work well for providing the required porosity of the filter element 10, preferably in a relatively loose, nonwoven state. Fibrous materials have been found to work quite well with the present invention, as they provide a relatively large surface area for their volume, while still allowing reasonably free air circulation therethrough. The use of fiber glass (or many other synthetic materials) is economical, and moreover is not as prone to mildew and other deterioration as many natural fibers are.

Figure 5:
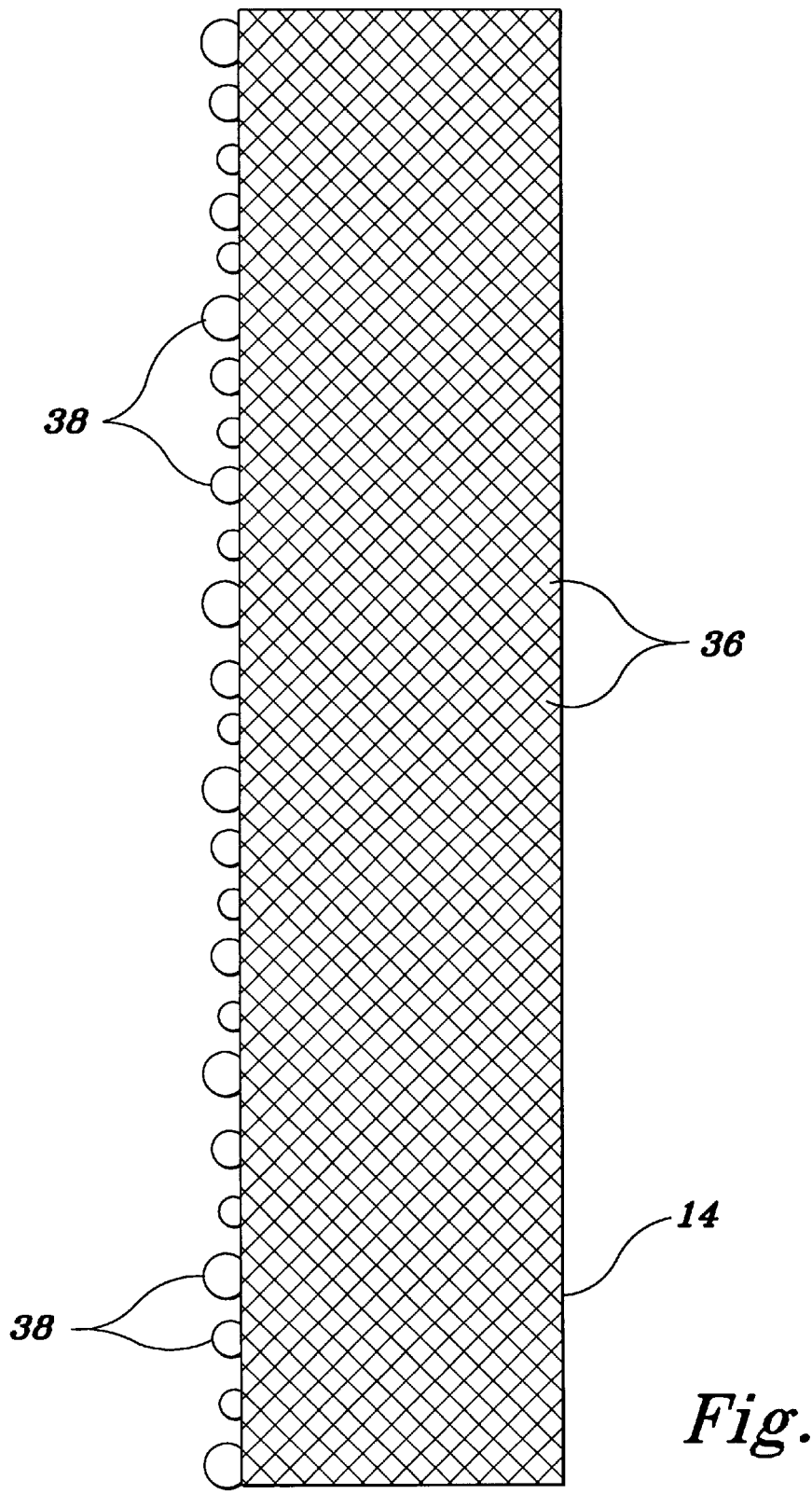
FIG. 5 is a side elevation view of a second embodiment filter element, with an exaggerated showing of the coating of the filter structure with odor adsorbent material.

The odor adsorbent chemical(s) used in the present invention preferably comprise a sodium bicarbonate (or related compound) or an activated carbon product (charcoal, etc.). These materials are well known for their adsorbent properties, and are quite economical. The present invention provides relatively high efficiency by coating the fibers of the woven or nonwoven filter element 14 with one or both of the above compounds, as desired, indicated by the stippling 38 of FIG. 4. The fibers 34 and 36 may be coated with a very thin adhesive blown through the filter element 10, with the adsorbent compounds being provided as a powder and blown through the filter element 10 to adhere to the adhesively coated fibers 34 and 36. Alternatively, the fibers 34 and 36 may be coated with a substance to capture the adsorbent compounds, before assembly into a filter element. In FIG. 5, a section of the filter element 14 is illustrated, with the application of the adsorbent material 38 being illustrated as bubbles on the surface.

Figure 6:
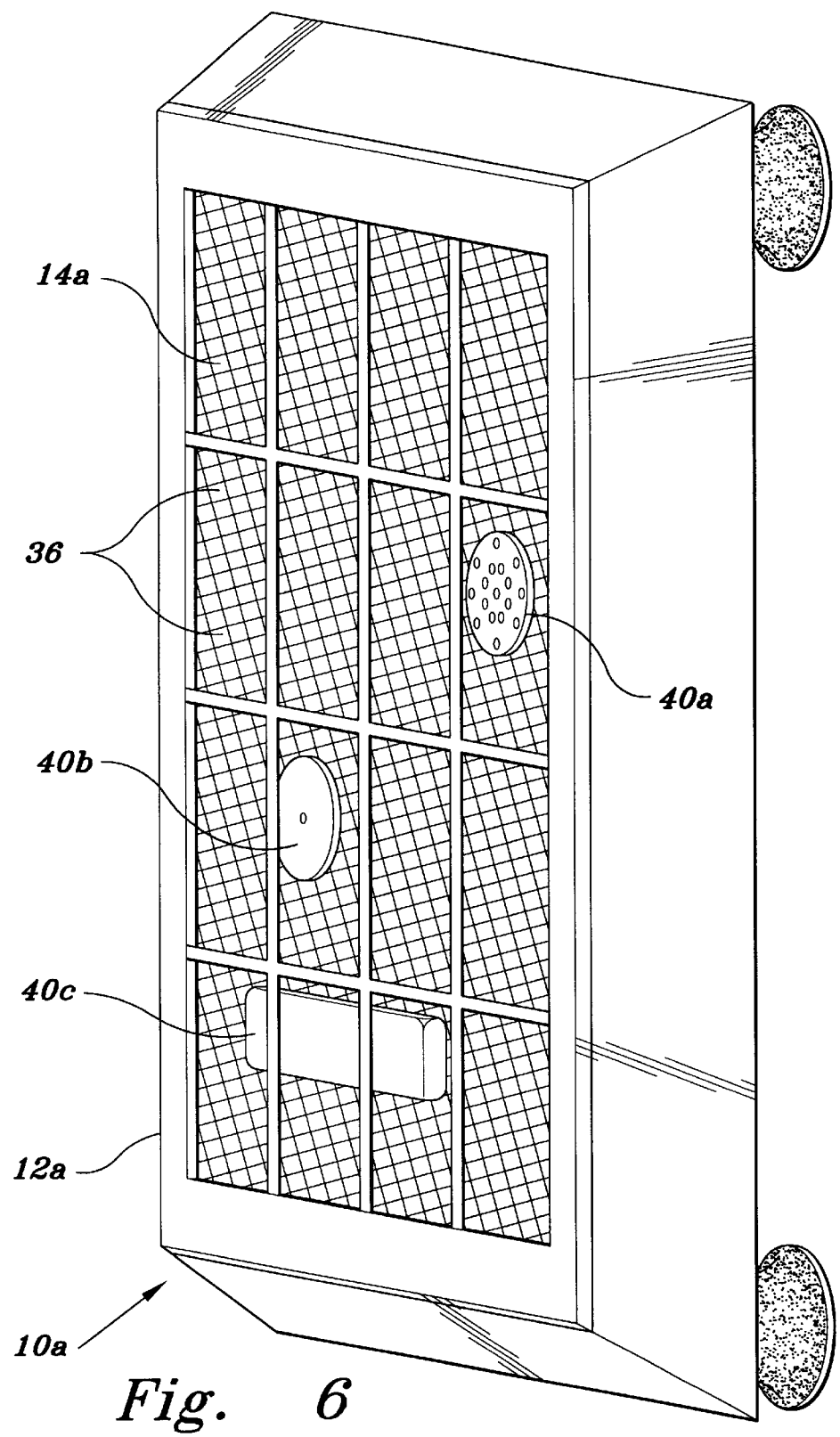
FIG. 6 is a perspective view of a second embodiment filter which may incorporate one of the filter elements of FIGS. 4 and 5.

FIG. 6 illustrates a somewhat different embodiment of the present invention, with the housing 12a comprising a somewhat taller configuration than that of the relatively square housing 12 of FIGS. 1 through 3. Accordingly, the filter element 14a contained therein has a similar size and shape in order to fill the interior of the housing 12a, although it is constructed in the same general manner, e.g., using a woven material 36 (or nonwoven material as used for the filter elements 14 of FIGS. 2 and 3).

The filter assembly 10a of FIG. 6 also differs in that a series of scented elements 40a through 40c therein, either affixed to the filter element 14a or captured or affixed within the housing 12a, as shown. Such scented elements may diffuse any of a number of different scents (e.g., floral, pine, herbal, citrus, etc.) as desired. Such scents are known in other fields (fabric softener sheets, etc.) and equivalent means may be applied to the present invention.

Figure 7:
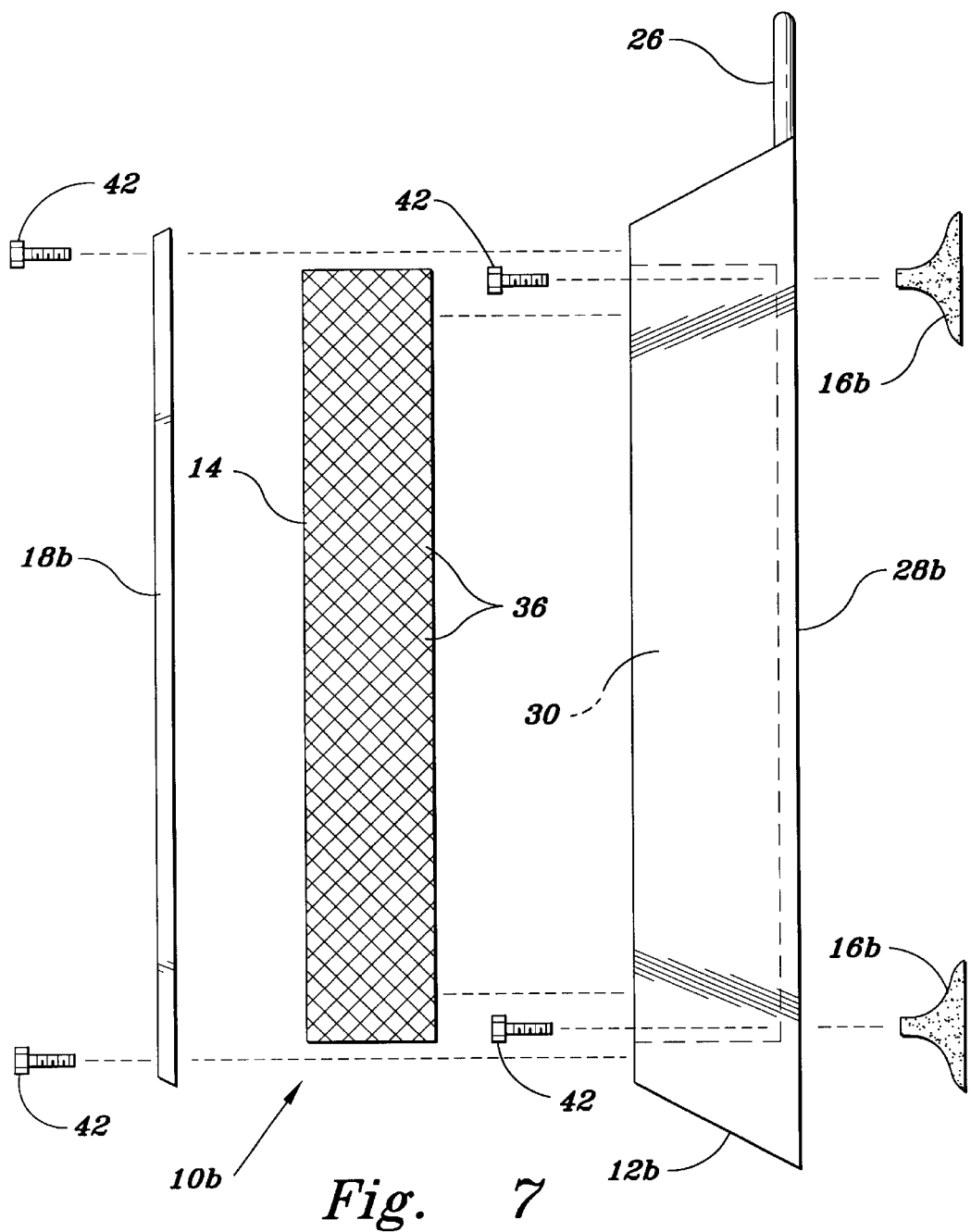
FIG. 7 is an exploded side elevation view of a third embodiment filter of the present invention, showing details thereof.

FIG. 7 illustrates another embodiment of the present invention, designated as filter assembly 10b. In this embodiment 10b, the front panel 18b is removably secured to the housing 12b by means of a series of threaded fasteners 42 (screws, bolts, etc.). In a like manner, the suction cups 16b are secured to the rear panel 28b by a series of threaded fasteners 42 (which may be the same size and configuration, or different, from those used to secure the front panel 18b to the housing 12b). In this embodiment, the front panel 18b is removed from the housing 12b for removal and replacement of the filter element 14 therein.

Figure 8:
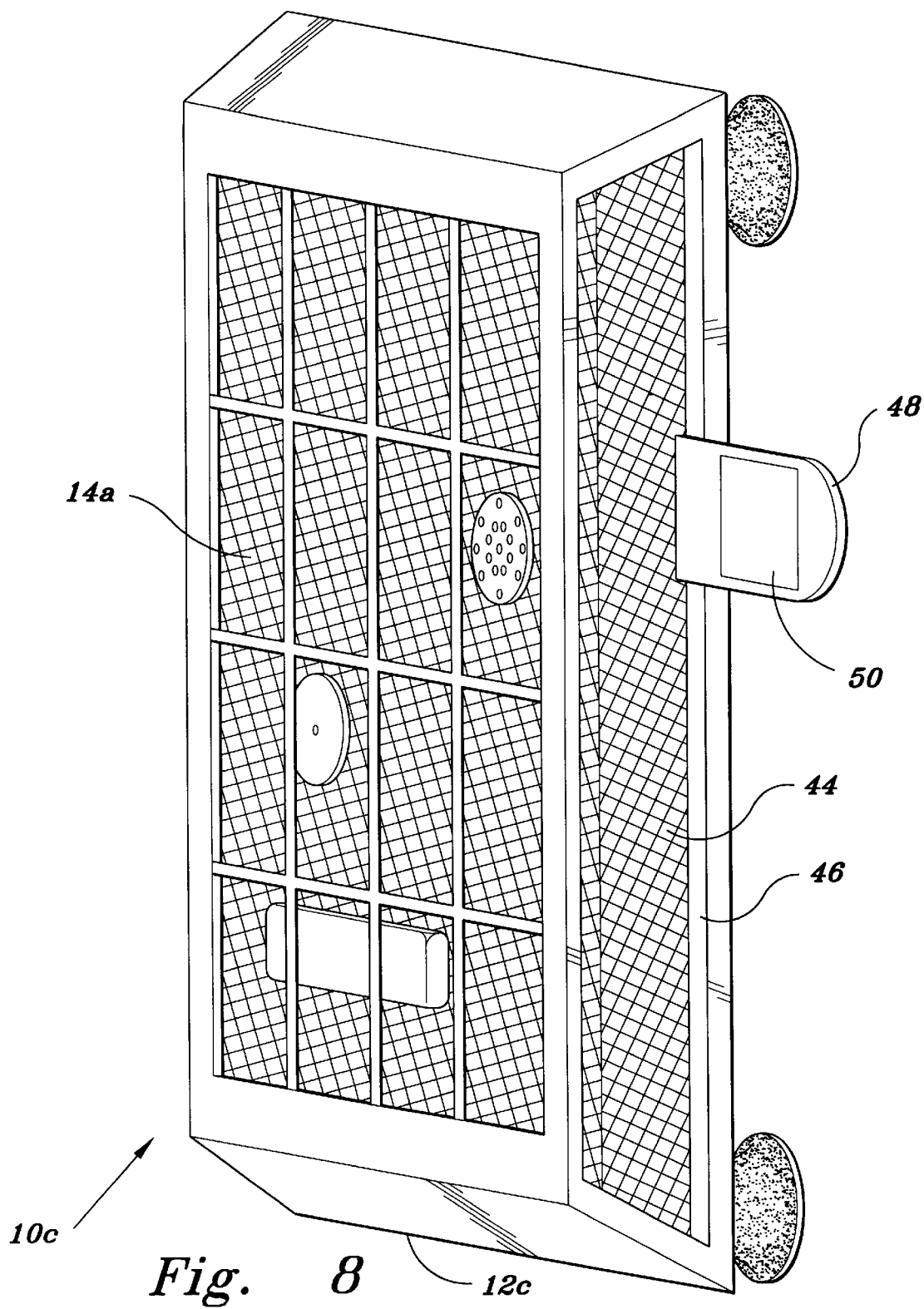
FIG. 8 is a perspective view of the filter device of FIG. 6, with a modified filter element including filter element replacement indicator means.

FIG. 8 illustrates yet another embodiment of the present invention, in which the filter housing 12c provides an easier means of removing and replacing the filter element 14a as desired. In FIG. 8, the housing filter assembly 10c includes an open side 44, exposing the filter element 14a therethrough. In the case of the filter assembly 10c, it is not necessary to access screws or other threaded fasteners in order to remove and replace the filter element 14a. Rather, the filter element 14a may be removed simply by withdrawing it from the housing 12c through the side opening 44, an acing with a fresh filter element 14a through the same opening 44. (A slightly raised lip 46 may be provided about the periphery of the opening 44, in order to retain the filter element 14a within the housing 12a.) Thus, the entire filter assembly 10c may remain in place within the refrigerator or other cold storage unit, without need for removal and replacement for accessing screws or other fasteners.

It is important that the various filter elements forming a major part of the present invention, provide a clear indication of the expiration or saturation of the adsorptive powers of the compounds contained therein. Accordingly, FIG. 8 also shows a tab 48 extending visibly from the side opening 44 of the assembly 10i c. This tab 48 includes a chemically treated indicator area 50 thereon which is readily visible, with the treated area 50 changing color as the adsorbent material becomes saturated. The area 50 may be formed of the same or similar compounds as those used to impregnate the filter elements of the present invention, and may be treated with a dye or the like which is affected chemically by the saturation of the adsorbent compounds. Other means of indicating the saturation of the adsorbent compounds may be used as desired, but such changes of color with changes in chemical composition or saturation are well known, as in litmus papers, carbon monoxide detectors, etc., with the present invention making use of such known technology in a new and unanticipated manner. The extended tab 48 also provides a convenient means for withdrawing a used filter element 14a from the housing 12c when required.

In summary, the present odor adsorptive filter provides a much improved means of controlling undesirable odors within a refrigerator, freezer, ice chest, or any other cold storage device as desired. The use of suction cups for removably securing the device to the interior wall panel of the refrigeration unit, eliminates need for shelf space previously required for conventional open boxes of baking soda and the like commonly used for the purpose. The filter of the present assembly is easily exchanged for a new unit when an old filter becomes saturated with odoriferous matter. Moreover, the filtration element of the present invention provides a much more efficient means of exposing the maximum surface area of the adsorbent chemicals to the ambient air within the refrigeration unit, by coating the fibers of the filter with the adsorbent material. Thus, the present odor adsorptive filter will be greatly appreciated by those who have ever experienced need for removing undesirable odors from a refrigerator, freezer, or other cold storage unit.

It is to be understood that the present invention is not limited to the embodiments described above, but encompasses any and all embodiments within the scope of the following claims.

I claim:

1. An odor adsorptive filter for adsorbing odoriferous matter from the ambient air in a cold storage unit, comprising:

a filter housing having at least a front panel, a rear panel opposite said front panel, and an interior for holding a filter element therein;

said front panel and said rear panel including at least one air circulation passage therethrough, for circulation of air through said interior of said filter housing;

a filter element removably disposed within said interior of said filter housing; and said filter element comprising a porous structural matrix holding at least one odor adsorbent chemical therein, for circulation of air therethrough.

2. The odor adsorptive filter according to claim 1, including means for temporarily and removably securing said filter housing to an inner surface of the cold storage unit.

3. The odor adsorptive filter according to claim 2, wherein said means for temporarily and removably securing said filter housing to an inner surface of the cold storage unit comprises a plurality of suction cups extending from said rear panel of said filter housing.

4. The odor adsorptive filter according to claim 1, wherein said at least one odor adsorbent chemical of said filter element is selected from the group consisting of sodium bicarbonate and activated carbon.

5. The odor adsorptive filter according to claim 1, including means for indicating the need for replacement of said filter element when said odor adsorbent chemical has been saturated with odoriferous matter.

6. The odor adsorptive filter according to claim 5, wherein said means for indicating the need for replacement of said filter element comprises a tab extending visibly from said filter element and said filter housing, with said tab including means for changing color when said tab is saturated with odoriferous matter.

7. The odor adsorptive filter according to claim 1, including means for distributing a pleasing scent to the ambient air.

8. An odor adsorptive filter for adsorbing odoriferous matter from the ambient air in a cold storage unit, comprising:

a filter housing having at least a front panel, a rear panel opposite said front panel, and an interior for holding a filter element therein;

said front panel and said rear panel including at least one air circulation passage therethrough, for circulation of air through said interior of said filter housing;

a filter element disposed within said interior of said filter housing;

said filter element comprising a porous structural matrix holding at least one odor adsorbent chemical therein, for circulation of air therethrough; and means for indicating need for replacement of said filter element when said odor adsorbent chemical has been saturated with odoriferous matter.

9. The odor adsorptive filter according to claim 8, wherein said means for indicating need for replacement of said filter element comprises a tab extending visibly from said filter element and said filter housing, with said tab including means for changing color when said tab is saturated with odoriferous matter.

10. The odor adsorptive filter according to claim 8, including means for temporarily and removably securing said filter housing to an inner surface of the cold storage unit.

11. The odor adsorptive filter according to claim 10, wherein said means for temporarily and removably securing said filter housing to an inner surface of the cold storage unit comprises a plurality of suction cups extending from said rear panel of said filter housing.

12. The odor adsorptive filter according to claim 8, including means for removably replacing said filter element within said filter housing.

13. The odor adsorptive filter according to claim 8, wherein said at least one odor adsorbent chemical of said filter element is selected from the group consisting of sodium bicarbonate and activated carbon.

14. The odor adsorptive filter according to claim 8, including means for distributing a pleasing scent to the ambient air.

15. An odor adsorptive filter for adsorbing odoriferous matter from the ambient air in a cold storage u comprising:
   a filter element comprising a porous matrix of fibers;
   at least one odor adsorbent chemical imbedded in and coating said fibers of said porous matrix, thereby providing max surface area exposure of said odor adsorbent chemical to ambient air; and
   a tab extending visibly from said filter element indicating the need for replacement of said filter element, said tab including means for changing color when said tab is saturated with odoriferous matter.

16. The odor adsorptive filter according to claim 15, wherein said at least one odor adsorbent chemical of said filter element is selected from the group consisting of sodium bicarbonate and activated carbon.

17. The odor adsorptive filter according to claim 15, wherein said porous matrix is formed of materials selected from the group consisting of woven and nonwoven fiberglass and other synthetic and natural fibers.

18. The odor adsorptive filter according to claim 15, including means for distributing a pleasing scent to the ambient air.

* * * * *